US008068616B2

(12) United States Patent
Copley et al.

(10) Patent No.: US 8,068,616 B2
(45) Date of Patent: Nov. 29, 2011

(54) METHODS AND SYSTEMS FOR CONTROLLING NOISE CANCELLATION

(75) Inventors: David C. Copley, Peoria, IL (US); Benjamin Mahonri Faber, Spanish Fork, UT (US); Scott D. Sommerfeldt, Mapleton, UT (US)

(73) Assignees: Caterpillar Inc., Peoria, IL (US); Brigham Young Universtiy, Provo, UT (US)

( * ) Notice: Subject to any disclaimer, the term of this patent is extended or adjusted under 35 U.S.C. 154(b) by 1311 days.

(21) Appl. No.: 11/646,417

(22) Filed: Dec. 28, 2006

(65) Prior Publication Data

US 2008/0159553 A1 Jul. 3, 2008

(51) Int. Cl.
*A61F 11/06* (2006.01)
*G10K 11/16* (2006.01)
*H04R 29/00* (2006.01)

(52) U.S. Cl. ........ 381/71.2; 381/71.1; 381/58; 381/94.1

(58) Field of Classification Search ...... 381/71.1–71.14, 381/93, 95, 96, 94.1, 58, 124
See application file for complete search history.

(56) References Cited

U.S. PATENT DOCUMENTS 4,987,598 A 1/1991 Eriksson
5,251,262 A 10/1993 Suzuki et al.
5,386,477 A 1/1995 Popovich et al.
5,499,302 A 3/1996 Nagami et al.
5,692,055 A 11/1997 Sano et al.
5,699,437 A 12/1997 Finn
5,724,432 A 3/1998 Bouvet et al.
5,768,124 A 6/1998 Stothers et al.
5,809,152 A * 9/1998 Nakamura et al. ........... 381/71.8
6,219,427 B1 4/2001 Kates et al.
6,266,422 B1 7/2001 Ikeda (Continued)

FOREIGN PATENT DOCUMENTS

EP 0 568 292 A3 11/1993

OTHER PUBLICATIONS

Hansen, C.H. et al., "Real Time Control of Sound Pressure and Energy Density in a Mining Vehicle Cabin", *Tenth International Congress on Sound and Vibration*, Jul. 7-10, 2003, Stockholm, Sweden, pp. 3713-3719.

(Continued)

*Primary Examiner* — Xu Mei
(74) *Attorney, Agent, or Firm* — Finnegan, Henderson, Farabow, Garrett & Dunner, L.L.P.

(57) ABSTRACT

A method for detecting failure in a noise cancellation system is provided. The noise cancellation system is operable to at least partially cancel an unwanted noise produced by a noise source. The method includes receiving a cancellation noise signal from the noise cancellation system. The cancellation noise signal represents a cancellation noise that, when combined with a target noise, is operable to at least partially cancel the target noise. The method also includes receiving an error signal approximately representing a portion of the target noise that remains after the cancellation noise and the target noise are combined. The method also includes determining whether the signal level changed or remains unchanged for each of the received cancellation noise signal and the error signal. The method also includes assigning a failure state of the noise cancellation system based on the determination and initiating a remedial measure that corresponds with the assigned failure state.

22 Claims, 4 Drawing Sheets

U.S. PATENT DOCUMENTS

| | | | | |
|---|---|---|---|---|
| 6,522,753 | B1 | 2/2003 | Matsuzawa et al. | |
| 6,594,365 | B1 | 7/2003 | Eatwell | |
| 7,103,188 | B1 * | 9/2006 | Jones | 381/71.9 |
| 7,106,866 | B2 | 9/2006 | Astorino et al. | |
| 7,248,708 | B2 * | 7/2007 | Vaudrey et al. | 381/94.7 |
| 7,792,312 | B2 * | 9/2010 | Inoue et al. | 381/71.9 |
| 2003/0219132 | A1 | 11/2003 | Sommerfeldt et al. | |
| 2004/0052383 | A1 | 3/2004 | Acero et al. | |

OTHER PUBLICATIONS

Faber, B. M., “Active Minimization of Acoustic Energy Density in Enclosed Sound Fields”, (unpublished M.S. thesis), Department of Physics and Astronomy, Brigham Young University, 2004, 73 pages.

* cited by examiner

METHODS AND SYSTEMS FOR CONTROLLING NOISE CANCELLATION

TECHNICAL FIELD

The present disclosure relates generally to environment control, and more particularly, to methods and systems for controlling noise cancellation.

BACKGROUND

Noisy environments may be uncomfortable and distracting, so it may be desirable to reduce the impact of unwanted noise from such environments. For example, in a passenger vehicle, it would be beneficial to minimize unwanted noises, such as road noise, in the vehicle's cabin to increase the comfort level for the passengers.

Noise cancellation systems may be used to reduce such unwanted noise (also referred to as "target noise") from an environment by generating a substantially contemporaneous cancellation noise having the same amplitude and frequency as the unwanted noise, but 180 degrees out-of-phase. As a consequence, when the sound waves of the two noises meet at a particular location, the two noises substantially cancel one another by destructive interference, which allows occupants of the environment to perceive less unwanted noise.

Noise cancellation systems, however, may fail for a variety of reasons. When failure occurs, the noise cancellation system may have no effect on the target noise and worse, may increase the amount of noise in the environment.

As disclosed in U.S. Pat. No. 5,809,152 ("the '152 patent) issued to Nakamura et al. on Sep. 15, 1998, an adaptive noise suppression system may be automatically disengaged when the system detects the amount of noise in a space is increasing. Specifically, the '152 patent discloses a noise suppression system including a phase and amplitude control device for determining a secondary sound for reducing noise in the space, microphones for detecting remaining noises in the noise space, a divergence prediction device for judging whether the secondary sounds are normal or are moving to an abnormal state, and a control stop device for preventing the output of the secondary sound. Based on predictions made by the divergence prediction device, the control stop device may automatically disengage the noise suppression system before a noise increase occurs.

The divergence prediction device disclosed by the '152 patent predicts whether the noise suppression system is diverging based on an error signal provided from noise in the space detected by the microphones. However, because the error signal includes whatever noises are received by the microphones, any unusual noises occurring in the space affect the accuracy of the divergence prediction device's determination. Accordingly, the divergence prediction device may disengage the noise suppression system when unusual noises occur in the space rather than, for example, due to the divergence of the system. In addition, because the noise suppression system disclosed by the '152 patent only predicts divergence, the system does not consider other potential failure states that may affect the system and, therefore, cannot implement other remedial measures corresponding to the different failure states.

The disclosed methods and systems for noise cancellation are directed to overcoming one or more of the problems set forth above.

SUMMARY OF THE INVENTION

In some embodiments, a method for detecting failure in a noise cancellation system is provided. The noise cancellation system is operable to at least partially cancel an unwanted noise produced by a noise source. The method includes receiving a cancellation noise signal from the noise cancellation system. The cancellation noise signal represents a cancellation noise that, when combined with a target noise, is operable to at least partially cancel the target noise. The method also includes receiving an error signal approximately representing a portion of the target noise that remains after the cancellation noise and the target noise are combined. The method also includes determining whether the signal level changed or remains unchanged for each of the received cancellation noise signal and the error signal. The method also includes assigning a failure state of the noise cancellation system based on the determination and initiating a remedial measure that corresponds with the assigned failure state.

It is to be understood that both the foregoing general description and the following detailed description are exemplary and explanatory only, and are not restrictive of the invention, as claimed.

DETAILED DESCRIPTION

Figure 1:
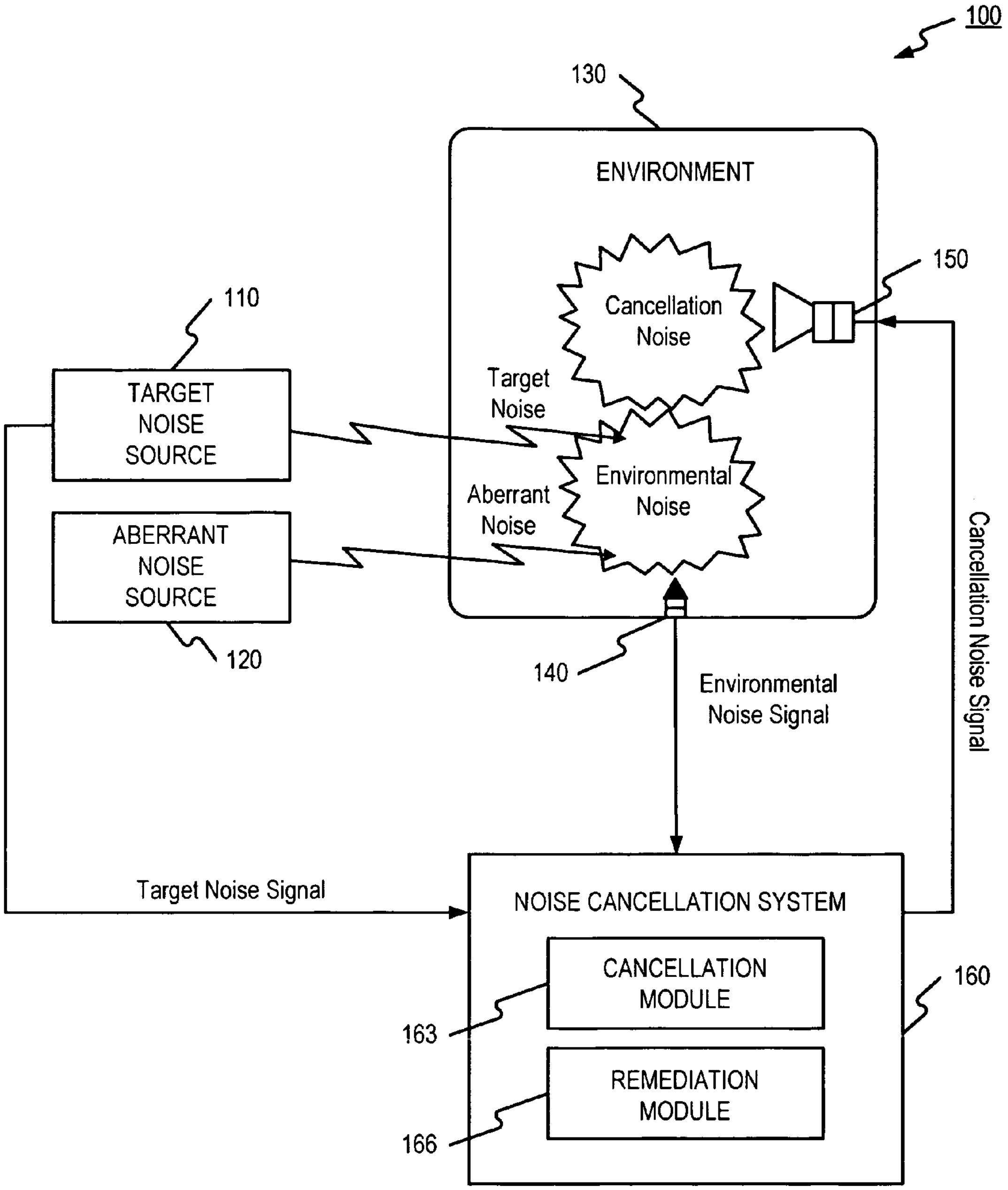
FIG. 1 is a block diagram illustrating an exemplary system environment consistent with embodiments disclosed herein.

FIG. 1 is a block diagram illustrating an exemplary system 100 that may benefit from some embodiments of the present disclosure. Exemplary system 100 may be, for instance, a vehicle equipped with an active noise cancellation system for cancelling noises in the vehicle's passenger compartment. However, any environment where noise may be present may benefit from some embodiments of the present invention. As shown in FIG. 1, system 100 may include a target noise source 110, an aberrant noise source 120, an environment 130, a sound input device 140, a sound output device 150, and a noise cancellation system 160.

Target noise source 110 may be an object or event that generates an unwanted target noise present in environment 130 and contributes to environment noise. Target noise source 110 may be located either inside or outside the defined environment 130, and in some cases, the target noise produced by target noise source 110 may be periodic or cyclical. A target noise signal may be a signal representing the characteristics of the actual target noise and provided from target noise source 110 to noise cancellation system 160 for determining a cancellation noise. For instance, target noise source 110 may be an engine system within a vehicle and the target noise signal may be obtained by a sensor communicatively coupled to a flywheel in the engine system and represent the frequency of the noise generated by the engine's reciprocating movement.

Aberrant noise source 120 may be an object or event that creates an aberrant noise also contributing to the environment noise in the environment 130. In some instances, the aberrant noise is an unexpected sound that may occur randomly, erratically, and/or transiently. Unlike the target noise, the aberrant noise is a generally non-cyclical and non-periodic noise such as the sound of a door slamming shut. However, in some instances, the aberrant noise may also be periodic, non-random, and predictable.

In some cases, environment 130 is a predefined space having known dimensions and acoustic characteristics in which the target noise is to be at least partially cancelled from the environment noise. Environment 130 in some embodiments may be a passenger compartment of an automobile, truck, train, or airplane. In other embodiments, environment 130 may be an operator's cabin in a construction vehicle, such as an excavator, wheel loader, backhoe loader and other environments in which an operator controls machinery. However, environment 130 is not limited to vehicles and may be any physically or conceptually defined space including a room, a building, a tunnel, or the like.

Generally, the contribution of target noise by target noise source 110 to environment noise may be predicted, and noise cancellation system 160 may estimate, at least in part, the environment noise received by sound input device 140. For example, the target noise signal may be obtained from a magnetic sensor coupled to an engine's flywheel or from a microphone located near the engine. Based on the target noise signal, noise cancellation system 160 may estimate or predict the engine noise that would be actually perceived in the passenger cabin of the vehicle at different engine speeds. In some cases, the estimation or prediction is implemented using a model representing the physical sound path or paths between the engine and one or more locations in the cabin where perception of sound is relevant. An example of the location may be the approximate location or area where an operator's ears may be located and/or where the sound-sensing input microphones of an active noise cancellation system may be positioned. One skilled in the art may determine other suitable locations to use as an end point of a physical sound path to be modeled.

Sound input device 140 includes one or more devices for receiving sound waves and converting the sound waves into electrical signals. In some instances, sound input device 140 may be one or more microphones mounted in various locations of environment 130. In other instances, sound input device 140 may be a multi-dimensional acoustic energy density sensor, such as two or three dimensional acoustic energy density sensors. Consistent with certain disclosed embodiments, sound input device 140 receives environment noise from environment 130 and provides a resulting environment noise signal to noise cancellation system 160. The environment noise may include the target noise and/or aberrant noise, among other noises.

Sound output device 150 includes devices for generating noises in environment 130 including, for example, one or more amplifiers, loudspeakers and/or other sound transducers for converting electrical signals into sound waves. For example, sound output device 150 may be a multi-dimensional sound system having several speakers mounted around various locations in a vehicle's passenger cabin. In some instances, sound output devices 150 may be part of a vehicle's existing audio system, such as an automobile stereo system. Noises generated by the sound output device 150 typically include audible sounds for cancelling noises from environment 130. However, sound output device 150 may also generate noises having frequencies outside the typical audible range for reducing, for example, vibrations affecting a vehicle and its occupants. Sound output device 150 may receive a cancellation noise signal from noise cancellation system 160 and, based on the cancellation noise signal, generate a cancellation noise for completely removing or at least reducing the target noise from the environment noise in environment 130. For instance, the cancellation noise may be the noise produced by a loudspeaker in the passenger cabin of a vehicle based on a noise cancellation signal provided by the noise cancellation system 160 to reduce the engine noise in the cabin.

Noise cancellation system 160 may include hardware and software modules operable to receive the target noise signal from target noise source 110 and to determine an appropriate cancellation noise signal. Noise cancellation system 160 may include a cancellation module 163 and a remediation module 166. Cancellation module 163 generates the cancellation noise signal based on the target noise signal received from target noise source 110. Cancellation module 163 provides the cancellation noise signal to sound output device 150 for cancelling the target noise occurring in environment 130. In addition, the cancellation noise signal may be provided to remediation module 166 for determining failure states of noise cancellation 160. Additional details are provided below in conjunction with FIGS. 2 and 3.

Remediation module 166 may determine whether noise cancellation system 160 is in one of several predefined failure states. As described in more detail below, remediation module 166 may detect failure states based on the cancellation noise signal and an error signal. If a failure state is determined, remediation module 166 may initiate one or more remedial responses corresponding to that failure state. For instance, remediation module 166 may initiate the deactivation of noise cancellation system 160 when it is determined that noise cancellation system 160 has become unstable. Or, if the failure state indicated is tolerable, the initiated measure may be to ignore the failure state.

As illustrated in FIG. 1, consistent with certain embodiments disclosed herein, target noise source 110 and/or aberrant noise source 120 may generate the target noise and the aberrant noise, respectively, that contribute to the environment noise. Noise cancellation system 160 may receive the target noise signal from target noise source 110 indicative of the target noise, and in response generate a cancellation noise signal. Audio output device 150 receives cancellation noise signal from noise cancellation system 160 and generates a cancellation noise for cancelling the target noise and thereby reducing environment noise. Consequently, an individual in environment 130 may be provided a quieter and/or less distracting environment.

In some embodiments, noise cancellation system 160 may receive environment noise signal from sound input device 140 indicative of environment noise in environment 130 and including the portion of target noise not cancelled by the cancellation noise. Based on the target noise signal received from target noise source 110 and the environment noise signal received from sound input device 140, noise cancellation system 160 may dynamically adjust the cancellation noise signal for improved cancellation of the target noise. In addition, based in part on these signals, noise cancellation system 160 may determine whether the system is in a failure state and initiate corresponding remedial measures.

Figure 2:
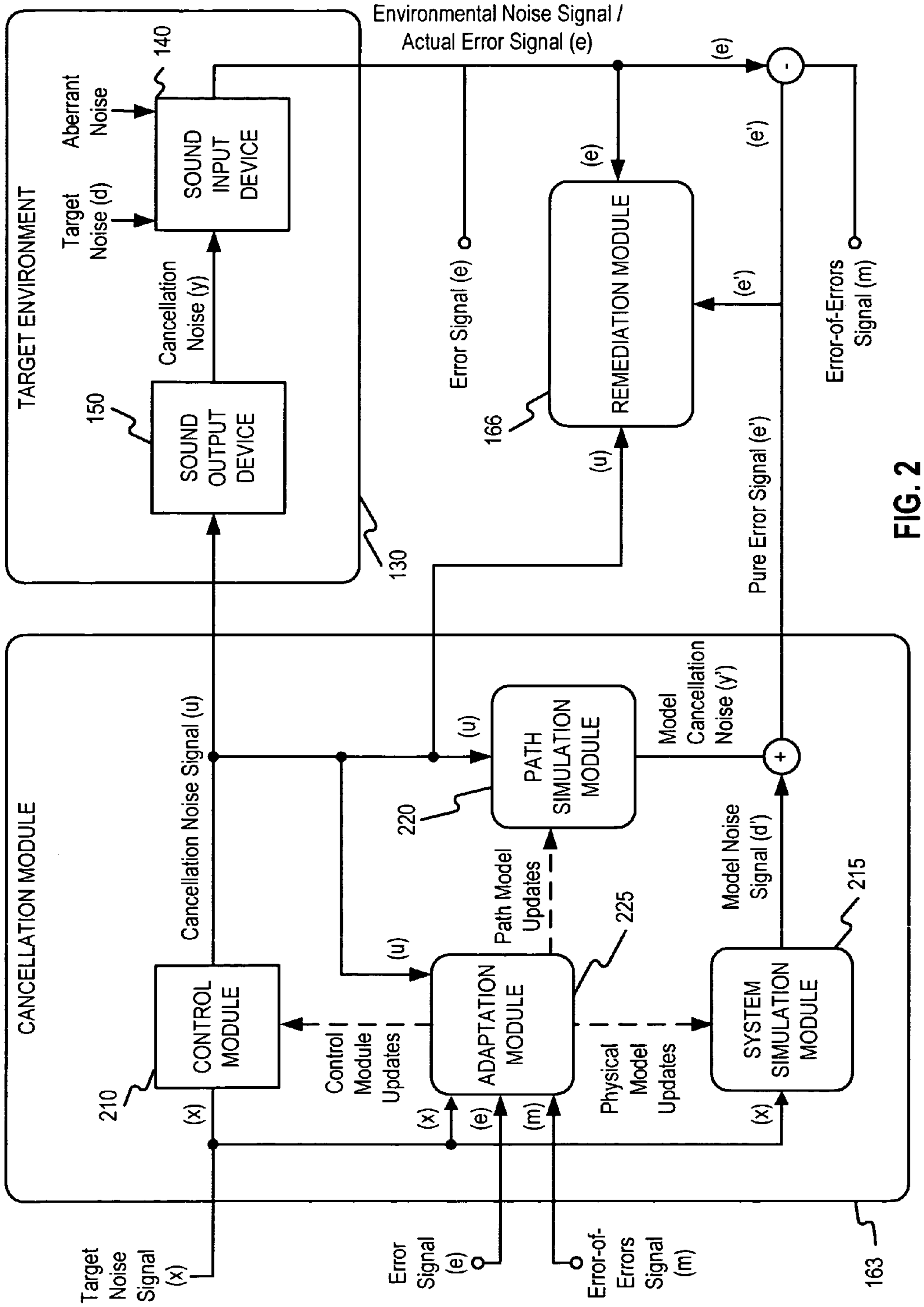
FIG. 2 is a block diagram illustrating an exemplary noise cancellation system.

FIG. 2 is a block diagram illustrating exemplary noise cancellation system 160. FIG. 2 illustrates the aforementioned environment 130, sound input device 140, sound output device 150, cancellation module 163, and remediation module 166. As also illustrated in FIG. 2, cancellation module 163 may include a control module 210, a system simulation module 215, a path simulation module 220, and an adaptation module 225.

Control module 210 may be a device operable to receive target noise signal (x) and determine a corresponding cancellation noise signal (u) for at least partially canceling target noise (d) in environment 130. Control module 210 may include a digital signal processor (DSP) having a microprocessor operable to execute signal conditioning algorithms for generating cancellation noise signal (u) based on the target noise signal (x), as is known in the art. In some embodiments, control module 210 may include an adaptive digital filter (e.g., finite impulse response filter or infinite impulse response filter), which, in some embodiments, is operable to adjust the various modifiable parameters that configure the amplitude and frequency of cancellation noise signal (u), thereby enabling the signal to be adapted to different target noises and/or changes in a target noise over time. These changes may be detected through sound input device 140.

System simulation module 215 may include computer-readable instructions operable to generate a model noise signal (d') that estimates or predicts target noise (d) present in environment 130. In particular, system simulation module 215 estimates the target noise (d) within the environment 130 using a model of system 100 that simulates the change in target noise as a result of the noise's travel along a path from target noise source 110 to a location in environment 130, where the target noise is received by sound input device 140 as part of the environment noise. The system model may be created using typical modeling software known in the art, such as SIMULINK, commercially available from The MathWorks, Inc., or the like. The system model may be, for instance, a physical path transfer function that estimates the target noise (d) occurring in environment 130 based on target noise signal (x) and takes into account the effect of materials, air, temperature, and other relevant characteristics of the physical path on the target noise (d) when it traveled between target noise source 110 and a particular location in environment 130, such as sound input device 140. In a vehicle, for example, system module 215 may estimate the engine noise that will result in the vehicle's passenger cabin by calculating the change in engine noise as it travels through an engine bay, vehicle body, and passenger cabin where the noise is received at a microphone.

Path simulation module 220, based on cancellation noise signal (u), may include computer-readable instructions operable to determine a model cancellation noise (y') that is an estimate of cancellation noise (y) generated by sound output device 150. Path simulation module 220 may determine model cancellation noise (y') from a path model that estimates the change in cancellation noise signal (u) due to the signal's travel from control module 210 to a particular location within environment 130, such as sound input device 140. An exemplary path model may also be created using known software for generating models, such as SIMULINK, as known in the art. The path model may simulate the various converters, filters, amplifiers, loudspeakers, microphones, air, temperature, and/or other relevant characteristics that alter cancellation noise signal (u) between the source of the cancellation noise signal (u) to where the signal is received again by cancellation module 163 through sound input device 140.

In some embodiments, cancellation module 163 may, using a summing circuit or the like, combine model noise signal (d') with model cancellation noise (y') to determine a pure error signal (e'). In some embodiments, pure error signal (e') represents only the remaining portion of the target noise signal that was not cancelled by the cancellation noise signal (u), and does not represent any other remaining noise. Pure error signal (e') may also be used to determine failure states of noise cancellation system 160, as explained below. In some embodiments, pure error signal (e') may also be provided to adaptation module 225 for updating parameters and/or coefficients of control module 210. In some embodiments, pure error signal (e') may be compared to actual error signal (e) to determine a value indicating an "error-of-errors," which can be used for improving the performance of system simulation module 215 and path simulation module 220. Additional details concerning the pure error signal (e') and "error-of-errors" value are provided below in conjunction with FIGS. 3 and 4.

Adaptation module 225 includes computer-readable instructions operable to update control module 210, system simulation module 215 and/or path simulation module 220 based, in part, on pure error signal (e'), error-of-errors value (m), target noise signal (x) and cancellation noise signal (u). For instance, using techniques known in the art, adaptation module 225 may determine updated control coefficients of the digital filter in control module 210. In addition, adaptation module 225 may update the parameters of the system model and path model included in the system simulation module 215 and path simulation module 220, respectively. In some embodiments, by actively updating these modules using pure error (e') rather than actual error value (e) determined from sounds received by sound input device 140 from within environment 130, improved updates may be made to the control module 210, simulation module 215 and/or path simulation module 220. In some embodiments, this is because pure error signal (e') does not account for aberrant noises or other environmental noise, which allows the determination of the performance efficiency of control module 210.

According to some disclosed embodiments, remediation module 166 includes a computer-readable program operable to determine whether noise cancellation system 160 is in one of several possible failure states and initiate one or more remedial measures for noise cancellation system 160 corresponding to an assigned failure state. Using cancellation noise signal (u) and pure error signal (e'), remediation module 166 may determine whether noise cancellation system 160 is in, for instance, a tolerable failure state, output calibration failure state, or an instability failure state. Based on this determination, remediation module 166 may initiate one or more corresponding remedial measures, such as ignoring the failure, activating a warning indicator, resetting noise cancellation system 160 to an initial state, recalibrating the output of noise cancellation system 160, changing coefficients used in control module 210, deactivating adaptation module 225, and/or deactivating noise cancellation system 160.

From monitoring the signal level of cancellation noise signal (u) and pure error signal (e'), for example, remediation module 166 may determine that noise cancellation system 160 is unstable and initiate the activation of an indicator light and gradual deactivation of noise cancellation system 160. In some embodiments, based on error signal (e), remediation module 166 may determine that noise control system 160 is in another failure state and, as a result, selectively deactivate adaptation module 225 and/or noise cancellation system 160. Making determinations of whether noise cancellation system 130 is in a failure state based on pure error signal (e') determined from the path and simulation models, rather than making the determination based on actual error value (e), leads to certain advantages. For example, the accuracy of failure determinations may be improved since pure error value (e') is indicative of the target noise remaining in environment 130 but excludes actual noises occurring in environment 130 (e.g., aberrant noise) that might otherwise lead to an incorrect determination that noise cancellation system 160 is in a failure state.

Although one embodiment for determining pure error value (e') is described herein, other embodiments may use different methods of approximating the target noise remaining after the noise cancellation operation has been performed. In some embodiments, any value indicating the performance level of noise cancellation may be used in place of pure error value (e').

As illustrated in FIG. 2, consistent with one exemplary embodiment, control module 210 may receive target noise signal (x) from target noise source 110. Using target noise signal (x), control module 210 may determine cancellation noise signal (u) operable to at least partially cancel target noise (d) from environment noise in environment 130. The resulting cancellation noise signal (u) is then provided to environment 130 and converted into cancellation noise (y) used by sound output device 150.

After cancellation noise (y) is provided to environment 130 by sound output device 150, the resulting environment noise may be received by sound input device 140. Error signal (e) represents the remaining environment noise captured by sound input device 140 and includes portions of target noise (d) that cancellation noise (y) fails to cancel, as well as any additional noise, such as aberrant noise, that is also not cancelled by cancellation noise (y). In some embodiments, error signal (e) may be used as pure error signal (e') to the extent that error signal (e) sufficiently represents the uncancelled portion of the target noise signal. For example, this may occur where non-target noises are sufficiently low compared to the signal level of the target noise. Referring again to FIG. 2, in some embodiments, error signal (e) may be provided to remediation module 166 for use in determining an "error of errors," which is the comparison between the pure error signal (e') and error signal (e), and the "error of errors" value is used to update system simulation module 215 and/or path simulation module 220. In addition, error signal (e) may be provided to the adaptation module 225. Based on actual error (e), adaptation module 225 may, for example, modify coefficients and gains of the digital filter algorithm in control module 210 to reduce the actual error signal (e).

Concurrently or subsequently with the determination of cancellation noise signal (u), system simulation module 215 may determine model noise signal (d') based on target noise signal (x) using a model simulating a sound path traveled by target noise (x) from target noise source 110 to sound input device 140 within environment 130. Similarly, path simulation module 220 may determine model cancellation noise signal (y') using a model simulating a signal path traveled by cancellation noise signal (u) from noise cancellation module 160, through environment 130, and back to noise cancellation module 160.

After determining model noise signal (d'), cancellation module 163 may combine model noise signal (d') and model cancellation noise signal (y') to determine the pure error signal (e'). As described above, pure error signal (e') represents the portion of model noise signal (d') that is not cancelled by cancellation noise signal (u). Since pure error signal (e') is based on a model simulating a target noise, it does not represent any other noises not cancelled by cancellation noise, such as any aberrant noises that may be present in environment 130. Accordingly, based on this "pure error," remediation module 166 may make accurate determinations of whether noise cancellation system 160 is in a failure mode.

Furthermore, by subtracting pure error signal (e') from error signal (e), noise cancellation system 160 may determine a so-called error-of-errors signal (m) representing the difference between actual error (e) achieved by the noise cancellation signal in the environment 130 and pure error signal (e') achieved by cancellation noise signal (u) based on model noise signal (d'). In some embodiments, error-of-errors (m) is provided to adaptation module 225 for use in updating the models in system simulation module 215 and path simulation module 220.

Based on the error-of-errors signal (m), adaptation module 225 may adaptively reconfigure cancellation noise signal (u) produced by control module 210. In other words, adaptation module 225 may cause coefficients of the digital filter algorithm executed by control module 225 to be updated based on a change in error signal (e) and/or pure error (e'). For instance, remediation module 166 may determine whether the signal level of error signal (e) has changed or remains unchanged and, when it is determined that the level of error signal (e) has increased and exceeded at least one predetermined threshold for less than a predetermined time period, remediation module may initiate a measure deactivating adaptation module 225, but without deactivating the entire noise cancellation system.

INDUSTRIAL APPLICABILITY

Embodiments consistent with those disclosed herein may be applied in any type of vehicle, building, room, or other defined space. The disclosed embodiments may detect errors in a noise cancellation system, which allows appropriate corresponding remedial measures to be initiated. The operation of noise cancellation system 160 will now be explained.

Figure 3:
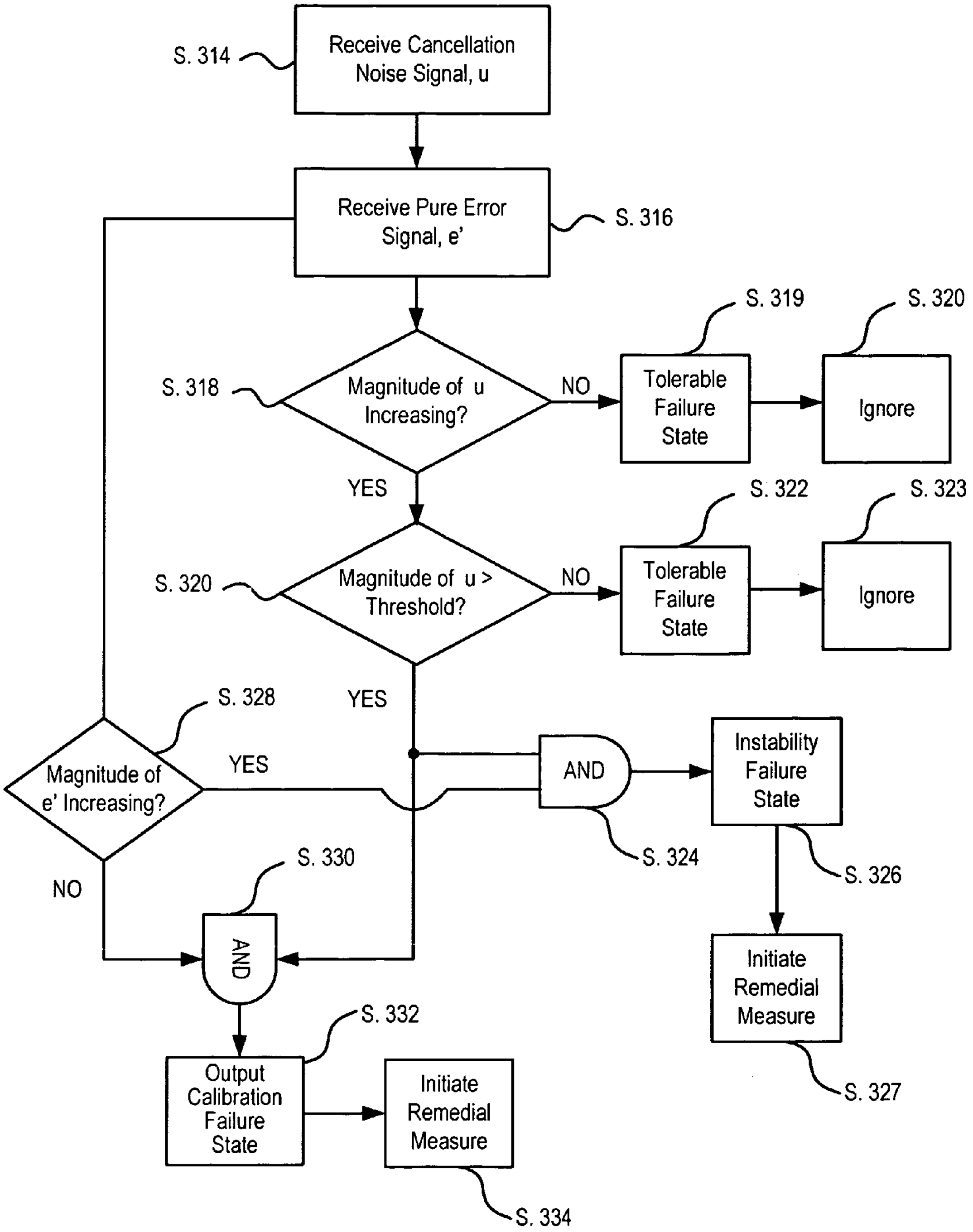
FIG. 3 is a flow chart illustrating an exemplary method of controlling noise cancellation.

FIG. 3 is a flow chart illustrating an exemplary method of controlling noise cancellation. As illustrated in FIG. 3, during operation of noise cancellation system 160, remediation module 166 receives cancellation noise signal (u) from cancellation module 163 representing a sound for canceling target noise (d) occurring in environment 130 due to target noise source 110. (Step-314) Remediation module 166 also receives pure error signal (e') representing the combination of model noise signal (d') determined by system simulation model 215 and model cancellation noise (y') determined by path simulation module 220. (Step-316) Based on a cancellation noise value indicative of a magnitude of cancellation noise signal (u) and the error value indicative of a magnitude of pure error signal (e'), in some embodiments, remediation module 166 determines whether noise cancellation system 160 is experiencing a failure state and may initiate one or more corresponding remedial responses to the determined failure state.

The magnitudes of cancellation noise signal (u) and pure error signal (e') may be, for example, a root-mean-square of the respective signals (e.g., $u_{rms}$ or $x_{rms}$) determined over a predetermined time frame. Concurrently or separately, remediation module 166 determines whether cancellation noise value and pure error value are increasing over time. This determination may be made by comparing a current signal value with one or more corresponding signal values sampled from the signals over a particular time period. For instance, remediation module 166 may determine whether the signals are increasing by calculating a slope of cancellation noise values or error values sampled over two or more time increments.

When the cancellation noise value is not increasing (step-318, NO), remediation module 166 may determine that noise cancellation system 160 is in a tolerable failure state (step-319) and ignore the condition without initiating a remedial response (step-320). If, however, noise cancellation value is increasing (step-318, YES), remediation module 166 may determine whether the noise cancellation value exceeds a predetermined threshold value (step-320). When the cancellation noise value is increasing and is less than the predetermined threshold value (step-320, NO), remediation module 166 may determine the condition of the noise cancellation unit to be a tolerable failure state (step-322) and ignore the condition without activating a remedial response. (Step-323) The predetermined threshold may be set at different levels depending on the particular application for which the noise cancellation is being used. For instance, noise cancellation system 160 may be calibrated to set the threshold lower for an automobile than for an aircraft.

In some embodiments, remediation module 166 determines a failure state based on the value of cancellation noise value and the pure error value. Specifically, remediation module 166 may determine that, simultaneously, the cancellation noise value is increasing (step-318, YES), that the cancellation noise value is greater than the threshold value (step-320, YES), and that the error value is increasing (step-328, YES). In this event, remediation module 166 may judge the failure state of noise cancellation system 160 to be an instability failure (step-326). Based on this determination, remediation module 166 may activate one or more remedial measures (step-327), such as initiating a failure warning indication, modifying coefficients of control module 210, and/or shutting down the noise cancellation system 160. In some embodiments, deactivation of the noise cancellation system 160 may be performed gradually over a period of time to avoid abrupt changes in the environment noise. In some embodiments, this is advantageous because the occupant of environment 130 may not notice a change in the perceived noise level.

However, remediation module 166 may determine that the cancellation noise value is increasing (step-318, YES), and that the cancellation noise value is greater than the threshold value (step-320, YES), but that the pure error value is not increasing (step-328, NO). In this event, remediation module 166 may judge that the failure state is an output calibration failure (step-332). In this state, remediation module 166 may activate one or more remedial measures (step-334), such as recalibration, initiating a failure warning indication, and/or shutting down the noise cancellation system 160. In some cases, the deactivation may be temporary while, for example, a recalibration is performed. And, as above, the deactivation of noise cancellation system 160 may be performed gradually to avoid abrupt changes in the environment noise.

Figure 4:
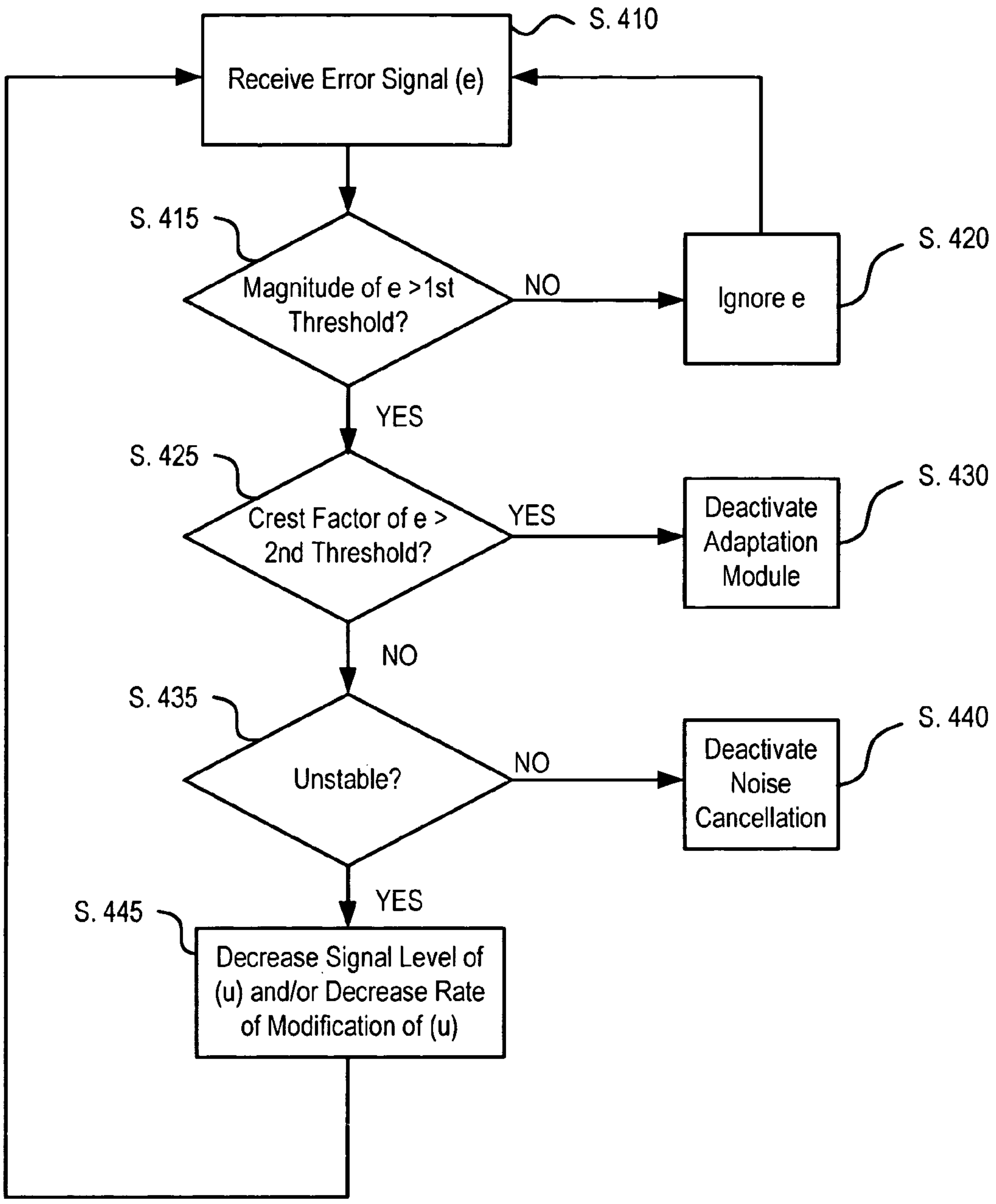
FIG. 4 is a flow chart illustrating an exemplary method of controlling noise cancellation.

FIG. 4 is a flow chart illustrating another exemplary method of controlling noise cancellation. Remediation module 166 may receive error signal (e) received from sound input device 140 representing the environmental noise remaining in target environment 160 after sound output unit 150 provides the cancellation noise signal (y) into the target environment 130 for cancelling the target noise (d). (Step-410). In other words, error signal (e) represents the environment noise, including the portion of the target noise, that is not cancelled by the cancellation noise. By analyzing error signal (e), remediation module 166, in some embodiments, determines whether noise cancellation system 160 is experiencing a failure state and may initiate one or more remedial responses corresponding to the determined failure state.

In particular, remediation module 166 may determine whether the magnitude of error signal (e) exceeds a first threshold criteria for greater than a predetermined amount of time. The level of error signal (e) may be determined by calculating a root-mean-square of error signal (e) representing the magnitude of error signal (e) over a predetermined time frame. In some embodiments, the root-mean-square may be a weighted average of an error signal (e) sample during the predetermined time frame such that more recent samples are given greater weight than earlier values in the resulting root-mean-square value of error signal (e). The time-frame for sampling error signal (e) may be selected based on the particular application or environment in which the noise cancellation system 160 is used. For instance, in a vehicle, the length of the time-frame value may be 0.125 seconds corresponding approximately to the duration of noise generated by a slamming door.

In addition, the first criteria may be a threshold value indicative of the maximum noise-handling capacity of noise cancellation system 160, such as the signal level at which the error signal (e) is clipped by the noise cancellation system 160. For the purposes of disclosed embodiments, "clipping" means that a signal level exceeds the maximum operating capacity of a component. For instance, clipping may occur when the maximum signal input or output range of a microphone, filter, or amplifier is exceeded by a large noise signal causing some or all components of error noise signal (e) to be cut-off above a certain signal level.

Remediation module 166 may determine whether or not the level of error signal (e) is greater than a first threshold criteria. (Step-415) If remediation module 166 determines the level of error signal (e) is not greater than the threshold criteria (Step-415, NO), remediation module 166 may determine to ignore the error signal (e) and continue operation without initiating a remedial measure (step-420). For example, if noise cancellation system 160 is operating properly, noise occurring in environment 130 may be sufficiently cancelled so that the resulting environmental noise is too soft and/or too short in duration to cause error signal (e) to exceed the first threshold criteria. Accordingly, remediation module 166 may ignore the error signal rather than initiating some remedial measure.

However, when the level of error signal (e) magnitude exceeds the first threshold criteria (step-415, YES), remediation module 166 may then determine whether error signal (e) exceeds a second threshold criteria (step-425). The second criteria may be, for example, indicative of whether the above-described clipping is due to an aberrant noise, an input calibration problem, and/or an instability problem of noise cancellation system 160. In some embodiments, the second threshold criteria may be a crest factor of error signal (e). As used herein, a crest factor refers to a ratio of a signal's amplitude to signal's effective or average value. For instance, the crest factor in some embodiments may be a value calculated from the ratio between the peak value of error signal (e) and the root-mean-square value of (e).

Using the crest factor, remediation module 166 may determine the extent that error signal (e) is clipped. In some embodiments, a signal having a crest factor equaling 1.0 (i.e., peak value is equal to root-mean-square value) may indicate that error signal (e) is being continuously clipped. A higher crest value (i.e., peak value is greater than root-mean-square value) may indicate a proportionally lower clipping of error signal (e). In some embodiments, when error signal (e) has a crest factor greater than 5.0, this may indicate normal (or at least tolerable) operation of noise cancellation system 160. On the other hand, a crest factor of error signal (e) in a range of 1.0 to 1.5 may indicate noise cancellation system 160 is in a failure state. Accordingly, a crest factor of error signal (e) that is at or below 1.5 may suggest that noise cancellation system 160 is experiencing input calibration problems or instability problems.

If error signal (e) exceeds the second threshold criteria for noise cancellation unit 160 (step-425, YES), error signal (e) may not be due to input calibration problems or instability problems of noise cancellation system 160. Instead, the cause of error signal (e) exceeding the first criteria may be an unusual or aberrant noise in environment 130. In some embodiments, this is determined by determining whether error signal (e) exceeds a crest factor threshold value. For example, if the crest factor of error signal (e) is above a predetermined crest factor threshold value, it is determined that the cause of the error signal (e) is not due to an input calibration problem or instability. In this case, remediation module 166 may select a remedial measure to deactivate the adaptation module 220 from updating parameters of digital filter in the noise control module 210. (Step-430) Even though the adaptation module 220 is deactivated, the noise cancellation unit 160 may continue to operate without receiving update parameters from the adaptation module 220. For instance, the noise may be an aberrant noise, such as a door slamming. Accordingly, in some embodiments, remediation module 166 may only deactivate adaptation module 225 temporarily to prevent adaptation module 225 from making unnecessary changes in cancellation noise signal (u) due to an aberrant noise that temporarily increases error signal (e). Once a predetermined time selected to allow such aberrant sounds to subside has elapsed, adaptation module 220 may be activated again, in some embodiments.

But if the level of error signal (e) does not exceed the second threshold criteria (step-425, NO), remediation module 166 may determine whether or not noise cancellation system 160 is unstable (step-435). The determination of whether noise cancellation system 160 is unstable may be determined using any typical measure of stability known in the art. As described above, for instance, noise cancellation system 160 may be in a unstable state when the level of control signal (u) is increasing over time and exceeds a threshold value and, concurrently, the level of pure error (e') is increasing over time.

If noise cancellation system 160 is determined to be stable (step-435, NO), then noise cancellation system 160 may be in an input failure state, and remediation module 166 may select a remedial measure that deactivates noise cancellation system 160 (step-440). As with previous embodiments, deactivation of noise cancellation system 160 may be performed by gradually reducing the output of noise cancellation system over a period of time to prevent sudden changes in the environment.

If, however, noise cancellation system 160 is determined to be unstable (step-435, YES), remediation module 166 may initiate a remedial measure that commands adaptation module 225 to decrease the signal level of the cancellation noise signal (u) (step-445). For instance adaptation module 225 may reduce the control coefficients of the noise cancellation algorithm of the digital filter in control module 210, which may cause noise cancellation system 160 to stabilize. If not, repeated reductions of the filter coefficients may cause noise cancellation system 160 to effectively deactivate noise cancellation system 160 by reducing the coefficients to a level such that noise cancellation signal (u) is essentially zero. Alternatively or additionally, adaptation module 225 may vary the rate at which control module 210 updates noise cancellation signal (u) to remediate the instability. Decreasing the rate at which control coefficients of control module 210 of are modified, for example, may result in, or at least assist in stabilizing noise cancellation system 160. Accordingly, if noise cancellation system 160 is in an unstable failure state, these remedial measures may prevent additional noise from being input into an environment from noise cancellation system 160 and enable the system to recover from instability.

While illustrative embodiments of the invention have been described herein, the scope of the invention includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as nonexclusive.

While certain features and embodiments of the invention have been described, other embodiments of the invention will be apparent to those skilled in the art from consideration of the specification and practice of the embodiments of the invention disclosed herein. Although exemplary embodiments have been described with regard to vehicle cabins, the present invention may be equally applicable to other noise cancellation environments including, for example, rooms or tunnels. Further, the steps of the disclosed methods may be modified in any manner, including by reordering steps and/or inserting or deleting steps, without departing from the principles of the invention. It is therefore intended that the specification and examples be considered as exemplary only, with a true scope and spirit of the invention being indicated by the following claims.

What is claimed is:

1. A method for detecting failure in a noise cancellation system operable to at least partially cancel an unwanted noise within a defined space, wherein the unwanted noise is produced by a target noise source located outside of the defined space, the method comprising:

sensing a target noise with a dedicated sensing device located at the target noise source, the sensing device configured to receive noise primarily from the target noise source;

receiving a cancellation noise signal from the noise cancellation system, the cancellation noise signal representing a cancellation noise that, when combined with the target noise in the defined space, is operable to at least partially cancel the target noise in the defined space;

receiving an error signal approximately representing a portion of the target noise remaining after the cancellation noise and the target noise are combined;

for each of the received cancellation noise signal and the error signal, determining whether the signal level changed or remains unchanged; and based on the determination, assigning a failure state of the noise cancellation system and initiating a remedial measure corresponding with the assigned failure state.

2. The method of claim 1, wherein receiving the error signal includes receiving a pure error signal determined by combining a first model representing only the cancellation noise signal and a second model representing only a target noise signal that represents the target noise.

3. The method of claim 1, wherein determining whether the signal level changed or remains unchanged comprises determining that the signal level of the cancellation noise signal is not increasing, and wherein assigning the failure state includes assigning a tolerable failure state; and wherein initiating a measure includes ignoring the assigned failure state.

4. The method of claim 1, wherein determining whether the signal level changed or remains unchanged comprises determining that the signal level of the cancellation noise signal is increasing, and further comprising determining that the signal level of the cancellation noise signal is below a predetermined threshold, wherein assigning the failure state includes assigning a tolerable failure state; and wherein initiating a measure includes ignoring the assigned failure state.

5. The method of claim 1, wherein determining whether the signal level changed or remains unchanged includes determining that the signal level of the cancellation noise signal is increasing and that the signal level of the error signal is increasing, and further comprising determining that the signal level of the cancellation noise signal is at a level greater than a predetermined threshold, wherein assigning the failure state includes assigning an instability failure state.

6. The method of claim 5, wherein initiating a measure includes gradually decreasing the signal level of the cancellation noise signal over a predetermined period of time.

7. The method of claim 5, wherein initiating a measure includes decreasing a rate of modification of the cancellation noise signal.

8. The method of claim 1, wherein determining whether the signal level changed or remains unchanged comprises determining that the signal level of the cancellation noise signal is increasing and that the signal level of the error signal is not increasing, and further comprising determining that the signal level of the cancellation signal is at a level greater than a predetermined threshold, wherein assigning the failure state includes assigning an output calibration error state.

9. The method of claim 8, wherein initiating a measure includes recalibrating the noise cancellation system.

10. The method of claim 1, wherein initiating a measure includes deactivating the noise cancellation system.

11. The method of claim 10, wherein deactivating the noise cancellation system includes gradually decreasing the signal level of the cancellation noise signal over a predetermined period of time.

12. The method of claim 1, wherein the noise cancellation system includes an adaptive adjustment unit operable to monitor the signal level of the error signal and, based on the monitoring, reduce the signal level of the error signal by adjusting at least one characteristic of a next cancellation noise signal, and wherein determining whether the signal level changed or remains unchanged includes determining that the signal level of the error signal has increased, and exceeded at least one predetermined threshold for a predetermined time period, and further comprising deactivating the adaptive adjustment unit without deactivating the entire noise cancellation system.

13. A system for detecting failure in a noise cancellation system, the noise cancellation system configured to at least partially cancel an environmental noise within an enclosed space, comprising:

a computer having a microprocessor and a computer-readable medium coupled to the microprocessor;

a sensing device located at a target noise source outside of the enclosed space, the sensing device dedicated to receiving a target noise from the target noise source; and a program stored in the computer-readable medium, the program, when executed by the microprocessor, operable to:

receive a cancellation noise signal from the noise cancellation system, the cancellation noise signal representing a cancellation noise that, when combined with the target noise in the enclosed space, is operable to at least partially cancel the target noise in the enclosed space;

receive an error signal approximately representing a portion of the target noise remaining after the cancellation noise and the target noise are combined;

determine whether the signal level changed or remains unchanged for each of the received cancellation noise signal and the error signal; and based on the determination, assign a failure state of the noise cancellation system and initiate a remedial measure corresponding with the assigned failure state.

14. The system of claim 13, wherein the received error signal is a pure error signal determined by combining a first model representing only the cancellation noise signal and a second model representing only a target noise signal that represents the target noise.

15. The system of claim 14, wherein the program is operable to determine that the signal level of the cancellation noise signal is increasing and that the signal level of the error signal is increasing, and the program is further operable to determine that the signal level of the cancellation noise signal is at a level greater than a predetermined threshold, wherein the failure state is an instability failure state.

16. The system of claim 15, wherein the remedial measure corresponding to the assigned instability failure state includes gradually decreasing the signal level of the cancellation noise signal over a predetermined period of time.

17. The system of claim 15, wherein the remedial measure corresponding to the assigned instability failure state includes decreasing a rate of modification of the cancellation noise signal.

18. The system of claim 13, wherein the program is operable to determine that the signal level of the cancellation noise signal is increasing and the signal level of the error signal is not increasing, and the program is further operable to determine that the signal level of the cancellation noise signal is at a level greater than a predetermined threshold, wherein the failure state is an output calibration error state.

19. The system of claim 13, wherein the program is operable to determine that the signal level of the cancellation noise signal is not increasing, wherein the failure state is a tolerable failure state and the remedial measure is ignoring the assigned failure state.

20. The system of claim 13, wherein the program is operable to determine that the signal level of the cancellation noise signal is increasing but below a predetermined threshold, and wherein the failure state is a tolerable failure state and the remedial measure is ignoring the assigned failure state.

21. The system of claim 13, wherein:

the noise cancellation system is operable to receive a target noise signal representing the target noise and, based on the received target noise signal, generate the cancellation noise signal, the noise cancellation system having an adaptive adjustment portion operable to monitor the signal level of the error signal and, based on the monitoring, reduce the signal level of the error signal by adjusting at least one characteristic of a next cancellation noise signal, wherein the program is operable to determine that the signal level of the error signal has increased and exceeded at least one predetermined threshold for a predetermined time period, and further operable to deactivate the adaptive adjustment portion without deactivating the entire noise cancellation system.

22. A method for detecting failure in an active noise cancellation system operable to at least partially cancel an unwanted noise in a compartment of a vehicle, the unwanted noise including a target noise produced by a target noise source located outside of the compartment, the method comprising:

sensing the target noise with a dedicated sensor disposed proximate the target noise source and remote from the compartment;

receiving a cancellation noise signal from the active noise cancellation system of the vehicle, the cancellation noise signal representing a cancellation noise that, when combined with the target noise in the compartment, is operable to substantially cancel the target noise;

receiving a pure error signal representing only the portion of the target noise remaining after the cancellation noise and the target noise are combined;

determining that the signal level of the cancellation noise signal is increasing and above a first threshold;

determining that the signal level of the pure error signal is increasing at a time when the signal level of the cancellation noise signal is increasing and above the first threshold;

indicating that the active noise cancellation system is unstable; and initiating at least a partial deactivation of the active noise cancellation system.

* * * * *